(12) United States Patent
Deane et al.

(10) Patent No.: US 10,881,285 B2
(45) Date of Patent: Jan. 5, 2021

(54) NETWORK FOR COLLABORATING PERSONAL CARE DEVICES

(71) Applicant: KONINKLIJKE PHILIPS N.V., Eindhoven (NL)

(72) Inventors: Steven Charles Deane, Cambridge (GB); Rim Helaoui, Eindhoven (NL); Amir Hussein Rmaile, Eindhoven (NL); Yekaterina Borisenko, Lynwood, WA (US); Vincent Jeanne, Migne Auxances (FR); Marinus Karel Johannes De Jager, Eindhoven (NL); Aleksandro Grabulov, Bellevue, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/348,270

(22) PCT Filed: Nov. 3, 2017

(86) PCT No.: PCT/EP2017/078112
§ 371 (c)(1),
(2) Date: May 8, 2019

(87) PCT Pub. No.: WO2018/086986
PCT Pub. Date: May 17, 2018

(65) Prior Publication Data
US 2019/0313892 A1  Oct. 17, 2019

Related U.S. Application Data

(60) Provisional application No. 62/419,554, filed on Nov. 9, 2016.

(51) Int. Cl.
*A61B 1/24* (2006.01)
*A46B 15/00* (2006.01)
(Continued)

(52) U.S. Cl.
CPC ............ *A61B 1/24* (2013.01); *A46B 15/0004* (2013.01); *A61B 5/746* (2013.01); *A61C 17/221* (2013.01)

(58) Field of Classification Search
CPC ..... A61C 17/221; A61C 15/046; A61C 17/16; A61C 17/22; A61C 17/224;
(Continued)

(56) References Cited

U.S. PATENT DOCUMENTS 6,731,213 B1 * 5/2004 Smith ................ A46B 15/0002
15/167.1
10,064,711 B1 * 9/2018 Richter .................... A41H 1/02
(Continued)

FOREIGN PATENT DOCUMENTS

CN      204048584 U      12/2014
KR      20150080258      7/2015
(Continued)

OTHER PUBLICATIONS

Hanioka et al: "Hemoglobin Concentration and Oxygen Saturation of Clinically Healthy and Inflamed Gingiva in Human Subjects"; J. Periodont Res 1990, 25:93-98.
(Continued)

*Primary Examiner* — Eric Blount

(57) ABSTRACT

A method (400) for modifying a user's oral care program. The method includes the steps of: (i) providing (410) a network (200) comprising a first personal care device (10a) in communication with a second personal care device (10b); (ii) cleaning (420) at least a portion of the oral cavity using the first personal care device; (iii) obtaining (440), while cleaning with the first personal care device, sensor data for the at least a portion of the oral cavity; (iv) communicating (450) the obtained sensor data to the second personal care device; and (v) modifying (460), based on the communi-
(Continued)

cated sensor data, a function of the second personal care device.

11 Claims, 4 Drawing Sheets

(51) Int. Cl.
    *A61B 5/00*     (2006.01)
    *A61C 17/22*     (2006.01)

(58) Field of Classification Search
    CPC .......... A61C 2204/005; A46B 15/0008; A46B 15/0002; A46B 2200/1066; A46B 15/001; G06F 19/3418
    USPC ...................................................... 340/573.1
    See application file for complete search history.

(56) References Cited

U.S. PATENT DOCUMENTS

| | | |
|---|---|---|
| 2002/0133308 A1 | 9/2002 | Lundell et al. |
| 2007/0182571 A1* | 8/2007 | Kennish ............. G09B 19/0076 340/573.1 |
| 2011/0294096 A1 | 12/2011 | deCastro et al. |
| 2012/0171657 A1 | 7/2012 | Ortins et al. |
| 2014/0250612 A1* | 9/2014 | Curry .................. A61C 17/221 15/22.1 |
| 2015/0127371 A1 | 5/2015 | Dykes et al. |
| 2016/0143718 A1* | 5/2016 | Serval .................. A61C 17/221 15/22.1 |
| 2017/0056146 A1* | 3/2017 | Boughorbel ....... A46B 15/0004 |
| 2018/0184796 A1* | 7/2018 | Balooch ................ A46B 9/023 |

FOREIGN PATENT DOCUMENTS

| | | |
|---|---|---|
| WO | 2010129755 A1 | 11/2010 |
| WO | 2014016718 A1 | 1/2014 |
| WO | 2016046701 A1 | 3/2016 |

OTHER PUBLICATIONS

Lobene et al: "A Modified Gingival Index for Use in Clinical Trials"; Clinical Preventive Dentistry, vol. 8, No. 1, Jan.-Feb. 1986, pp. 3-6.

PCT/EP2017/078112, ISR and Written Opinion, dated Jan. 29, 2018.

* cited by examiner

NETWORK FOR COLLABORATING PERSONAL CARE DEVICES

CROSS-REFERENCE TO PRIOR APPLICATIONS

This application is the U.S. National Phase application under 35 U.S.C. § 371 of International Application No. PCT/EP2017/078112, filed on Nov. 3, 2017, which claims the benefit of U.S. Provisional Patent Application No. 62/419,554, filed on Nov. 9, 2016. These applications are hereby incorporated by reference herein.

FIELD OF THE INVENTION

The present disclosure is directed generally to methods and systems for improving dental care using a network of intelligent collaborative personal care devices.

BACKGROUND

A daily oral hygiene routine may consist of different steps such as tooth brushing, interdental cleaning, tongue cleaning, and anti-microbial mouth rinsing. Research shows that failure to effectively carry out one or more steps of the daily oral hygiene routine can lead to gum and periodontal diseases, which have been linked to heart problems, diabetes, and numerous other serious medical issues. Among individuals who do regularly brush, improper brushing habits can result in poor coverage of brushing and thus surfaces that are not adequately cleaned.

There are many different products available to facilitate and enhance effective oral care. Electric toothbrushes, interdental flossers, and tongue cleaners are all sold to help users improve their daily oral hygiene routine. All of these products are intended to be complementary, and may be utilized in a specific order to achieve proper care goals. The recommended order may vary depending on the user, the oral hygiene professional, or a variety of other factors. Following the recommended order, however, is important since it is designed to optimize oral hygiene and minimize damage to oral surfaces. Just one example of recommended order may be: (1) interdental cleaning; (2) cleaning with a toothbrush; (3) tongue cleaning; and (4) mouth rinse.

Most consumers, however, tend to use their toothbrush to clean teeth as recommended, including once or twice daily, but skip or miss the other steps of the routine. Additionally, many consumers who do complete every step of the routine do not accomplish every goal effectively. Further, while consumers may receive feedback from any one device about a cleaning session, that information is not shared with or utilized by other devices in the same or subsequent cleaning session. Indeed, there is no communication among oral hygiene devices to facilitate or improve the user's oral care.

Accordingly, there is a continued need in the art for a network of intelligent collaborative personal care devices that share information about cleaning coverage and/or effectiveness in order to automatically improve the user's dental care.

SUMMARY OF THE INVENTION

The present disclosure is directed to inventive methods and systems for sharing data between a plurality of oral care devices to improve oral care. Applied to a network of connected oral care devices, the inventive methods and systems enable communication of oral care efficiency and routine, and thus improve oral care. The connected oral care devices share information about usage or non-usage of devices, the order of device usage, and the quality, duration, and/or effectiveness of specific devices by the user. With this information, the connected oral care devices can automatically adapt to achieve improved oral care for the user.

Generally in one aspect, a method for modifying a user's oral care program is provided. The method includes the steps of: (i) providing a network comprising a first personal care device and a second personal care device, where the first personal care device is in communication with the second personal care device; (ii) cleaning at least a portion of the oral cavity using the first personal care device; (iii) obtaining, while cleaning with the first personal care device, sensor data for the at least a portion of the oral cavity; (iv) communicating the obtained sensor data to the second personal care device; and (v) modifying, based on the communicated sensor data, a function of the second personal care device.

According to an embodiment, the modification is made to correct a deficiency in the user's oral cleaning identified via the obtained sensor data.

According to an embodiment, the network further includes a central hub configured to facilitate communication between the first personal care device and the second care device.

According to an embodiment, the network further includes an imaging device configured to obtain one or more images of the oral cavity.

According to an embodiment, the modification is made automatically by the second personal care device.

According to an embodiment, the modification is a notification to the user.

According to an aspect is a method for modifying a user's oral care program. The method includes the steps of: (i) providing a network comprising a first personal care device and an imaging device, wherein the first personal care device is in communication with the imaging device; (ii) obtaining an image of at least a portion of the oral cavity using the imaging device; (iii) communicating the obtained image to the first personal care device; and (iv) modifying, based on the communicated image, a function of the first personal care device.

According to an aspect is a system for modifying a user's oral care program. The system includes: (i) a first personal care device configured to obtain sensor data for at least a portion of the user's oral cavity; and (ii) a second personal care device in communication with the first personal care device; wherein the second personal care device is configured to receive the obtained sensor data from the first personal care device, and further configured to modify, based on the obtained sensor data, a function of the second personal care device.

According to an embodiment, the system further includes a central hub configured to facilitate communication between the first personal care device and the second care device According to an embodiment, the system further includes an imaging device configured to obtain one or more images of the oral cavity.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a method and system for sharing data between a plurality of oral care devices. More generally, Applicant has recognized and appreciated that it would be beneficial to provide a network of intelligent devices to monitor a user's oral care in order to provide an evaluation of the user's cleaning efficiency, technique, duration, and other parameters of the user's oral hygiene. Accordingly, the methods described or otherwise envisioned herein provide a collaborative network of oral care devices configured to communicate sensor data regarding the user's oral hygiene. According to an embodiment, one or more of the connected oral care devices automatically adapts to augment oral care in response to the communicated sensor data from other oral care devices.

A particular goal of utilization of the embodiments and implementations herein is to provide information about use of a personal care device such as an electric toothbrush, an interdental device, an electric shaver a skin cleaner, and or many other personal care devices.

Figure 1:
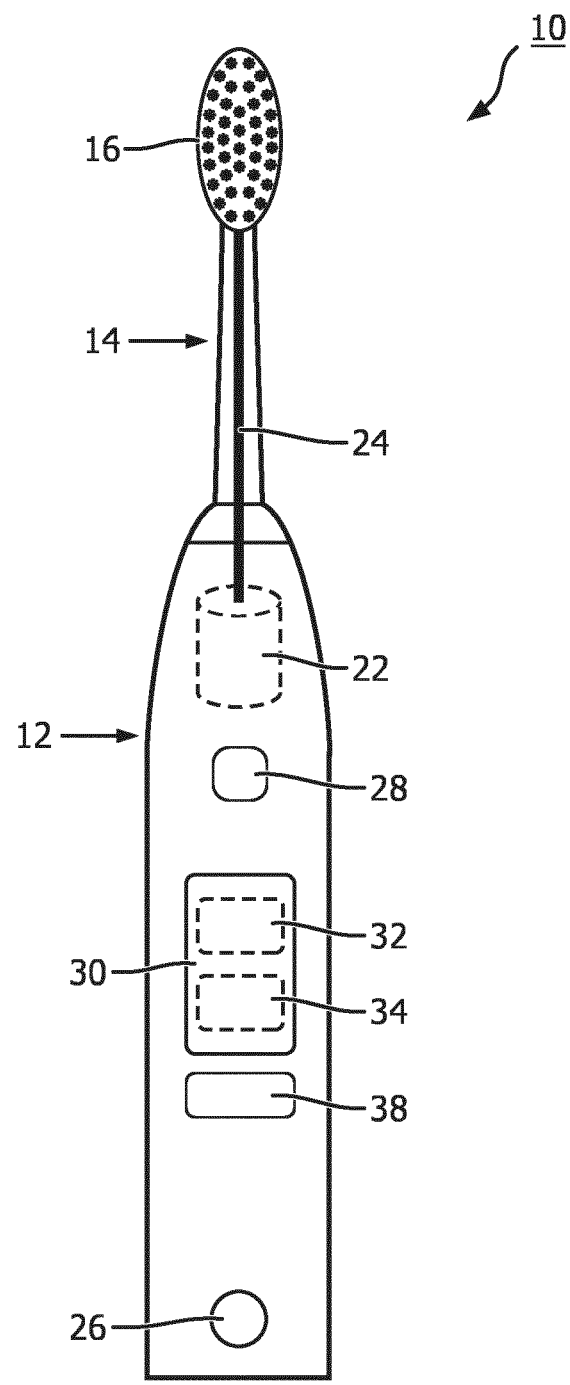
FIG. 1 is a representation of an oral care device in accordance with an embodiment.

Referring to FIG. 1, in one embodiment, personal care device 10 is provided that includes a body portion 12 and a head member 14. Head member 14 includes at its end remote from the body portion a head 16. The body portion 12 typically comprises a housing, at least a portion of which is hollow, to contain components of the personal care device. Head member 14 is mounted so as to be able to move relative to the body portion 12. The movement can be any of a variety of different movements, including vibrations or rotation, among others.

The body portion 12 typically contains a drivetrain assembly with a motor 22 for generating movement, and a transmission component or drivetrain shaft 24, for transmitting the generated movements to head member 14. For example, the drivetrain comprises a motor or electromagnet(s) 22 that generates movement of a drivetrain shaft 24, which is subsequently transmitted to the head member 14. The drivetrain can include components such as a power supply, an oscillator, and one or more electromagnets, among other components. In this embodiment the power supply comprises one or more rechargeable batteries, not shown, which can, for example, be electrically charged in a charging holder in which personal care device 10 is placed when not in use. According to one embodiment, head member 14 is mounted to the drive train shaft 24 so as to be able to vibrate relative to body portion 12. The head member 14 can be fixedly mounted onto drive train shaft 24, or it may alternatively be detachably mounted so that head member 14 can be replaced with a different brush head member for different operating features, or when a component of the head are worn out and require replacement.

The body portion 12 is further provided with a user input 26 to activate and de-activate the drivetrain. The user input 26 allows a user to operate the personal care device 10, for example to turn the device on and off. The user input 26 may, for example, be a button, touch screen, or switch.

Although in the embodiment shown in FIG. 1 the personal care device 10 is an electric toothbrush, it will be understood that in an alternative embodiment the personal care device is a manual toothbrush (not shown), a flossing device, an electric shaver, a skin cleaner, or other personal care devices.

Personal care device 10 includes one or more sensors 28. Sensor 28 is shown in FIG. 1 within body portion 12, but may be located anywhere within the device, including for example within head member 14 or head 16. Sensor 28 can comprise, for example, a 6-axis or a 9-axis spatial sensor system. For example, sensor 28 can be configured to provide readings of six axes of relative motion (three axes translation and three axes rotation), using for example a 3-axis gyroscope and a 3-axis accelerometer. As another example, sensor 28 is configured to provide the readings of nine axes of relative motion using, for example, 3-axis gyroscope, a 3-axis accelerometer, and a 3-axis magnetometer. Other sensors may be utilized either alone or in conjunction with these sensors, including but not limited to a pressure sensor and other types of sensors, such as a capacitive sensor, a camera, a photocell, a clock, a timer, and other types of sensors. Many different types of sensors could be utilized, as described or otherwise envisioned herein. According to an embodiment, sensor 28 is configured to generate information indicative of the acceleration and angular orientation of personal care device 10. The sensor may comprise two or more sensors 28 that function together.

Sensor data generated by sensor 28 is provided to a controller 30. Controller 30 may be formed of one or multiple modules, and is configured to operate the personal care device 10 in response to an input, such as input obtained via user input 26. Controller 30 can comprise, for example, a processor 32 and a memory 34. Processor 32 may take any suitable form, including but not limited to a microcontroller, multiple microcontrollers, circuitry, a single processor, or plural processors. Memory 34 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of personal care device 10. According to an embodiment, sensor 28 is integral to controller 30.

According to an embodiment, personal care device 10 comprises a communications module 38 that transmits collected sensor data, and can be any module, device, or means capable of transmitting a wired or wireless signal, including but not limited to a Wi-Fi, Bluetooth, near field communication, and/or cellular module.

Figure 2:
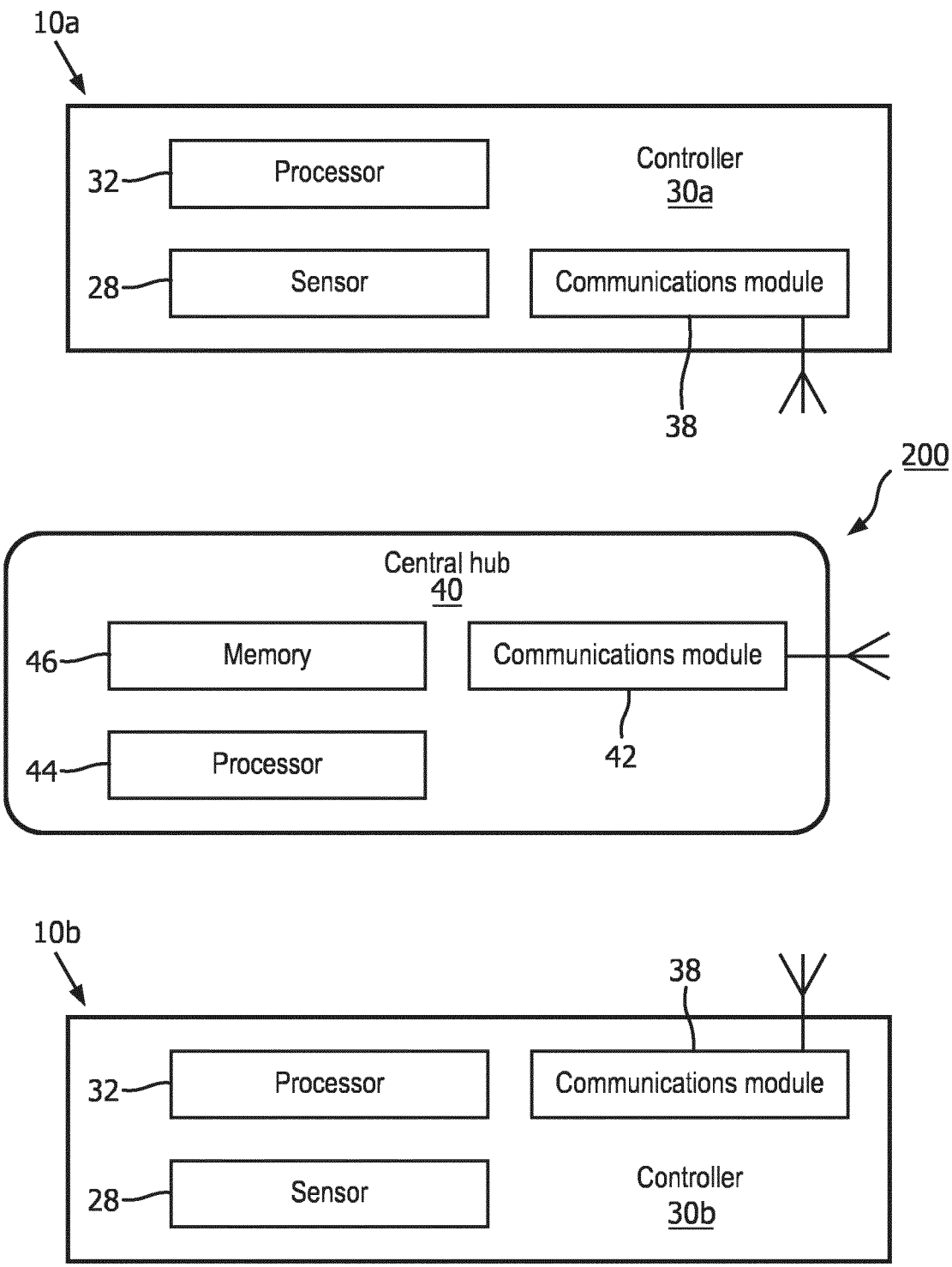
FIG. 2 is a schematic representation of an oral care device control system in accordance with an embodiment.

Referring to FIG. 2, an embodiment of a network 200 of intelligent collaborative personal care devices 10a and 10b is provided. According to an embodiment, each of the personal care devices 10a, 10b, comprises a controller 30, a processor 32, a sensor 28 which may be integral to the controller or merely in communication with the controller, and a communications module 38. Personal care devices 10a and 10b may be, for example, toothbrushes, interdental flossers, tongue cleaners, breath sensors, or any of a variety of other devices. Although network 200 in FIG. 2 includes only two devices personal care devices, it is appreciated that the network may comprise any number of personal care devices.

Network 200 optionally includes a central hub 40 which can be any device configured to or capable of receiving and processing sensor information transmitted from personal care devices 10a and 10b. Central hub 40 may be, for example, a base station or charging station for one or both of personal care devices 10a and 10b. Central hub 40 may alternatively be, for example, a local or remote computer or server. As another example, central hub 40 may be a hosted server or service available to the user online. Central hub 40 may also be a smartphone, wearable, tablet, or other portable computing device. Central hub 40 may be, for example, a smart bathroom mirror, or any other smart component.

According to an embodiment, central hub 40 includes a communications module 42 which can be any module, device, or means capable of receiving a wired or wireless signal, including but not limited to a Wi-Fi, Bluetooth, near field communication, and/or cellular module. Central hub 40 also includes a processor 44 which receives sensor information from sensor 28 of personal care devices 10a and 10b, or an analysis of the sensor data. According to an embodiment, device 40 may include a memory 46 to store received information from one or both of personal care devices 10a and 10b, or any other information.

According to an embodiment of system 200, personal care devices 10a and 10b can communicate with each other directly. Alternatively or in addition, personal care devices 10a and 10b are configured to communicate with central hub 40. According to another embodiment, one or both of personal care devices 10a and 10b only communicate with central hub 40. Many other configurations are possible.

As just one example, one or both of personal care devices 10a and 10b collects sensor information with sensor 28 and transmit that information locally via a Wi-Fi or Bluetooth connection to a smartphone device, where the sensor information is processed and/or stored. As another example, one or both of personal care devices 10a and 10b collects sensor information using sensor 28 and transmits that information via a Wi-Fi connection to the Internet where it is communicated to a remote server device 40. The remote server device 40 processes and/or stores the sensor information. A user may access that information directly or may receive reports, updates, or other information from the remote server device 40 or an associated device.

According to an embodiment, network 200 communicates information between one or more of personal care devices 10a and 10b and/or central hub 40, the information comprising data such as usage of a device, non-usage of a device, the order of usage of two or more devices, adherence to a prescribed or programmed personal care routine, quality of personal care such as efficiency or coverage of brushing, flossing, or tongue cleaning, and/or duration of brushing, flossing, or tongue cleaning. One or both of personal care devices 10a and 10b can utilize that information to modify its functioning, behavior, or other parameter. This modification may be an automated process. The modification could be as simple as reminding the user to go through the correct sequence when detecting that one or more devices were or are about to be skipped. More advanced modification might be to cause subsequent steps of the cleaning routine to compensate for weaknesses of one or more previous steps or routines. The following examples illustrate how information exchange within the network 200 among personal care devices 10 can improve the outcome of an oral cleaning routine.

Example 1

In this example, personal care device 10a is an electric toothbrush. It detects that the user under-brushed the upper left segment of the mouth in a brushing session. The toothbrush 10a shares this information with the base station 40. Base station 40 determines which of the other devices within the network 200 would best compensate for the brushing deficiency. Upon determining that the connected flosser 10b would be sufficient, the base station transmits a signal to the flosser 10b that it must focus extra attention on the left segment of the user's mouth.

Example 2

In this example, a networked breath sensor 10a detects that a user has bad breath of a particular intensity. The breath sensor shares this information with the base station 40. Base station 40 analyzes the received information, potentially comparing it to a predetermined threshold, and triggers an alarm or indication to use tongue cleaner 10b. The base station transmits a signal to the tongue cleaner to automatically adapt the tongue cleaning time. For example, the signal my indicate that the tongue cleaner should double or otherwise extend the cleaning time in response to the detected bad breath.

Example 3

In this example, a networked flosser device 10a detects gingivitis at specific interdental space. The flosser device shares this information, optionally including a location and the gingival index (GI), with the base station 40. Base station 40 analyses the received information, and determines which of the other devices in the system would best address the detected gingivitis. The base station transmits a signal to a toothbrush 10b which will adapt its amplitude, intensity, and/or brushing time to focus on the location where the gingivitis was detected.

Example 4

In this example, a networked mouthwash container or dispenser 10a detects that the user is using the mouthwash, including information such as whether the amount of mouthwash is sufficient, and/or whether the duration of rinsing was sufficient. The mouthwash container or dispenser communicates the information to the base station 40. The base station transmits a signal to the flosser 10b, which lowers its amplitude, intensity, and/or flossing burst duration time to minimize the damage that might happen to the enamel surface and prevent abrasion. Alternatively, the base station 40 and/or flosser 10b may trigger an alarm or indication to use a gentler flossing intensity.

According to an embodiment, the system 200 comprises an algorithm for analyzing sensor data and modifying the function of one or more devices within the network in order to maximize personal care. For general sequence checking and correction, the following algorithm can be used. Given a recommended sequence of personal hygiene steps involving n actions such as Action 1 (e.g., flossing with device 10a), Action 2 (e.g., brushing teeth with device 10b) and Action 3 (e.g., tongue cleaning with device 10c), the workflow can be described as follows: for each device 10a, 10b, and 10c, once it is held by the user to be used, the device communicates with the prior device in the sequence of oral hygiene steps to check whether that device has been used. If the prior device n has indeed been used, then the device or system provides a reminder to use device n+1. If the prior device has not yet been used, then the device or system provides a reminder to use device n−1. For example, when the user picks up the toothbrush 10a to start brushing the teeth, this action will trigger the flosser 10b to send out a reminder. This ensures that interdental cleaning accompanies tooth brushing. This builds or maintains a habit of doing both at the same time in one routine.

As just one example, the method or system may utilize the following algorithm to analyze sensor data and modify the function of one or more devices within the network in order to maximize oral care, although many other algorithms and methods are possible:

```
If user touches device n
then
        device n triggers the alarm of device (n+ 1) once the
        user is done with step 1.
If user touches device n with n > 1
Then
        While (n > 1)
                Device n sends a request to device (n−1) checking
                whether it has been used
                If yes
                then
                        If user is currently holding device n
                        Then
                                Device n triggers the alarm of device n+1
                                once the user is done using device n
                                Else trigger the alarm of device n.
                        Else n = n−1
        End while
End if
End if
Reset all device statuses
```

Example 5

In this example, interdental flosser 10a determines from one or more internal sensors that the device has not been utilized in five days. The interdental flosser shares this information with the base station 40, and/or the toothbrush 10b. Base station 40, for example, can determine which of the other devices within network 200 would best compensate for the flossing deficiency. Upon determining that the connected toothbrush 10b would be sufficient, the base station transmits a signal to the toothbrush 10b that subsequent brushing sessions must be longer and/or harder to compensate for the user's failure to use the interdental flosser.

Alternatively, base station 40 may determine that one or more of the personal care devices 10n has not been activated and/or communicated with the base station for a certain period of time. This period of time may be based on a pre-programmed or predetermined length of time, such as 24 hours, several days, or other times. In this embodiment, the base station need not receive information from the personal care device that it hasn't been utilized by the user; instead, the base station can determine this based on lack of communication or other activity from or by the personal care device. The base station may then determine which of the other devices within network 200 would best compensate for the deficiency.

Example 6

In this example, the personal device 10a determines the location within the oral cavity of a filling, crown, veneer, or other dental component using data from one or more sensors. The personal device shares this information with the base station 40, and/or another device 10b. Base station 40 transmits a signal to one or more other personal devices within the network indicating the location and/or identity of the dental component. The other personal devices can then modify their activity, duration, or other parameter to accommodate that information. For example, the other personal devices may reduce activity around the location of the identified dental component.

Example 7

In this example, personal device 10a uses data from one or more sensors to identify early caries, including the location of the caries. The personal device shares this information with the base station 40, and/or another device 10b. Base station 40 transmits a signal to one or more other personal devices within the network indicating the location of the dental caries. The other personal devices can then modify their activity, duration, or other parameter to accommodate that information. For example, the other personal devices may increase activity in the area of the caries in order to prevent further decay before professional assistance can be found.

Example 8

Gingivitis Detection and Correction

According to an embodiment, system or network 200 may be utilized to inform users that they have gingivitis, and to identify where in the mouth the gingivitis is located. Notably, gingivitis is readily corrected by proper oral care. Several techniques exist to detect gingivitis, although the information is fed to a user who must then take action to treat the gingivitis. However, the user may forget the location that needs extra care, particularly if feedback is given at the end of an oral care routine, and needs to take conscious action to provide extra oral cleaning to resolve the gingivitis.

According to an embodiment, system or network 200 can be configured to automatically modify an oral care routine in order to resolve detected gingivitis, potentially without any knowledge of the modification by a user. For example, the system may automatically increase the number of cleaning shots of an air- or liquid-shot flosser due to a detected gingivitis level, which can be delivered immediately or when the same location is treated in a subsequent oral cleaning routine. In a tooth brushing embodiment, the segment pacing signal or brushing intensity can be adjusted to ensure extra cleaning when gingivitis is detected. According to another embodiment the system modifies the operation of two or more devices in response to gingivitis detection.

According to another embodiment, detection of gingivitis by a device 10 within system or network 200 could automatically produce a change in amplitude or frequency of current or subsequent brushing action, and can also change the amount of time spent brushing each segment. For example, toothbrushes typically divide the oral cavity into four, six, or more sections or regions, and the user may be instructed to move onto a different section via a brief signal after a predetermined time. According to an embodiment, the segment timing may be determined at least in part by the determined gingivitis location and/or level. For example, the timing may be increased for region(s) where gingivitis was detected. According to another embodiment, an oral care-coaching software application (app) may have focus areas that can be determined or set by the user or a dental professional, and these could be configured or modified by a detected gingivitis location and/or level. The coaching app may include, for example, a final clean sweep stage, where the user is instructed as to which areas need extra attention. This functionality can be based on location, time, and detected gingivitis level.

According to another embodiment, detection of gingivitis by a device 10 within system or network 200 could automatically affect one or more parameters of an oral irrigator, including but not limited to water pressure, pulsation type, and/or spray pattern, such that cleaning is enhanced and simultaneously signaled in the problem area. The adjustment could be to a higher intensity level, to ensure more effective cleaning, or it could be to a more comfortable level due to potential sensitivity at an inflamed site, combined with a perceptible difference to signal to the user the need to linger and clean thoroughly.

According to an embodiment, a modification or direction may be repeated for a number of subsequent cleaning cycles, even if the gingivitis is apparently resolved. This may ensure, for example, that the condition is fully treated and does not return. Accordingly, system or network 200 can adaptively learn a user's trouble spots or methodology, and can adapt the current and/or future cleaning routine automatically to resolve the issue and/or to prevent recurrence of the issue.

Example 9

Connected Imaging Devices

According to an embodiment, system or network 200 may comprise or be in wired and/or wireless communication with an imaging device 10 configured to facilitate or enhance one or more functions of the system. For example, stained teeth are a concern or problem for many individuals, particularly for people that smoke or ingest coffee, tea, red wine, and other staining liquids or foods. Typically, these stains can be removed by additional brushing or the use of mildly abrasive toothpaste. Additionally, gingivitis is a problem for many adults. According to an embodiment of system or network 200, an image of the user's teeth can be utilized to detect gingivitis, determining remaining plaque, and/or analyze other oral conditions.

Figure 3:
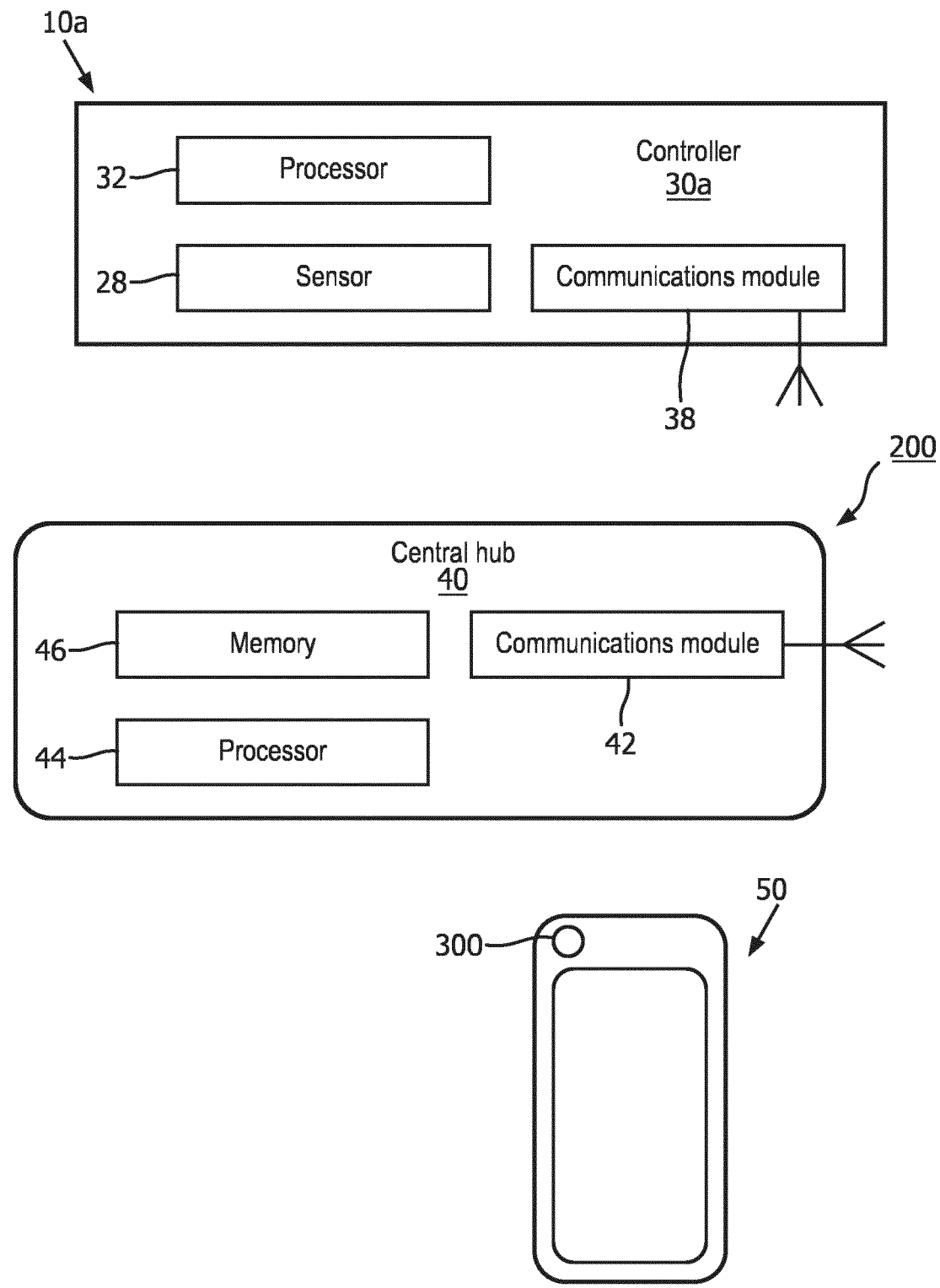
FIG. 3 is a schematic representation of an oral care device control system in accordance with an embodiment.

Referring to FIG. 3, an embodiment of system or network 200 comprising intelligent collaborative devices 10a and 10c and central hub 40 is provided. Device 10a is a personal care device such as a toothbrush, electric flossing device, tongue cleaner, mouthwash container, or other personal care device. Although FIG. 3 depicts a single personal care device, it is understood that system or network 200 may comprise multiple personal care devices. According to this embodiment, device 50 is an imaging device, such as a smartphone, configured to obtain one or more images of the user's mouth. Accordingly, device 50 comprises a camera 300. In addition to a smartphone, imaging device 50 may be a probe or other device configured to obtain one or more images of the user's mouth. For example, imaging device 50 may be incorporated into a toothbrush, electric flossing device, tongue cleaner, mouthwash container, or other personal care device. According to yet another example, device 50 may be a smart mirror, such as a bathroom mirror. Imaging device 50 may also be a wearable device, such as smart glasses (e.g., Google glasses). Additionally, the device may be a combination of two or more devices, such as a mirror and a camera, among many other combinations. Imaging device 50 obtains a photo and communicates the information to personal care device 10a and/or central hub 40. The photos may be analyzed by any of personal care device 10a, imaging device 50, and/or central hub 40, or a human examining the photos on any one of personal care device 10a, imaging device 50 and/or central hub 40. According to that analysis, the personal care device 10a can modify its functioning to address any issues identified in the one or more images. The modification may be automatic.

According to an embodiment, a user takes an image of the oral cavity, revealing as much of the front teeth and gums as possible. According to another embodiment, the image is obtained without user action, such as by a smart mirror in the bathroom. Multiple images may be obtained and stitched together to provide additional coverage of the oral cavity.

For example, if tooth staining is detected, a brushing routine can be automatically modified or created to provide a prolonged brushing time on the stained areas. Alternatively, the system may recommend to the user the use of a mildly abrasive and/or whitening toothpaste, or another home whitening product. Optionally, the system may provide functionality to order these products, or recommend local or online stores where they may be purchased. As another example, an electric flossing device may automatically increase the number of cleaning shots due to a gingivitis level detected by the imaging, which can be delivered immediately or when the same location is treated in a subsequent cleaning session.

According to another embodiment, the combination of an electronic-nose device and another device, such as smart glass, smart mirror, or camera, can distinguish malodor originating in the oral cavity from other malodors, and thus the oral care routine can be adjusted accordingly.

According to an embodiment, if the system determines over time that the modified oral care routine has been executed and the staining, gingivitis, or other condition is not resolved, then the system may further modify the oral care program or recommendations. For example, the system may recommend a visit to a dentist for a professional whitening treatment. The system may even automatically locate nearby practitioners and book an appointment for a whitening service.

Figure 4:
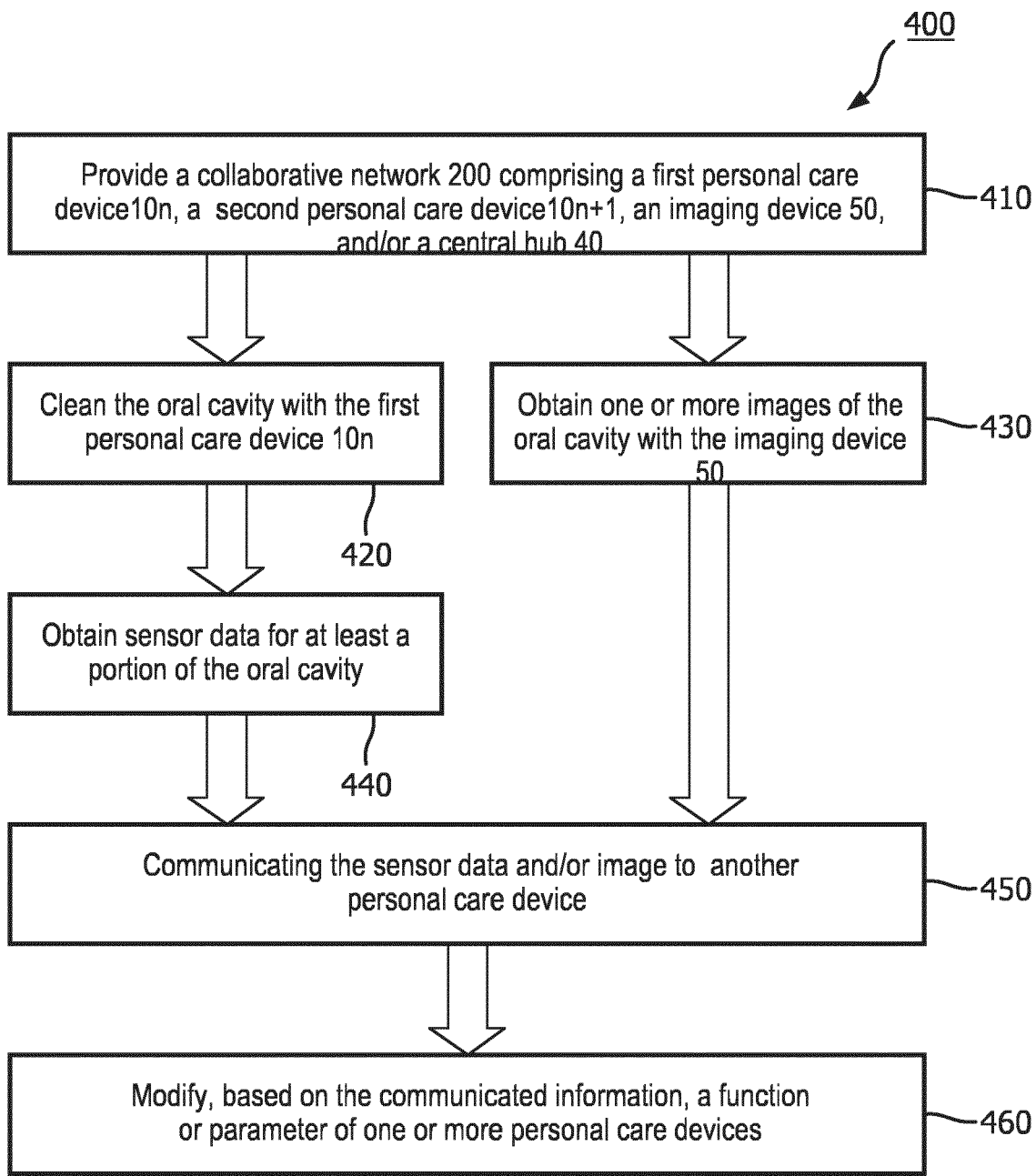
FIG. 4 is a flowchart depicting a method for communicating oral hygiene information within a network, in accordance with an embodiment.

Referring to FIG. 4, in one embodiment, is a flowchart of a method 400 for modifying a user's oral care, such as modifying an oral care program and/or an oral care device. At step 410 of the method, a network 200 of intelligent collaborative devices 10a, 10b, 10c, etc. is provided. The collaborative devices and network may be any of the embodiments described or otherwise envisioned herein. For example, according to one embodiment, the network comprises a first personal care device 10a, a second personal care device 10b, an imaging device 50, and/or a central hub 40.

At step 420 of the method, at least a portion of the user's oral cavity is cleaned using the first personal care device 10*a*. For example, the user may brush the teeth, floss, clean the tongue, use mouthwash, and/or otherwise clean the oral cavity.

According to another embodiment of the method, at step 430 of the method, the imaging device 50 obtains one or more images of the oral cavity. As described herein, the images may be actively obtained using a device such as a smartphone, and/or may be passively obtained using a device such as a smart mirror.

At step 440 of the method, the first personal care device obtains sensor data for at least a portion of the oral cavity during the cleaning session. For example, the personal care device may obtain sensor data about cleaning effectiveness or duration, about gingivitis, or about any other aspect of the oral cavity. As another example, sensor 28 may be a clock or a timer, and the personal care device may obtain sensor data about how long the oral cavity was cleaned, and/or how long certain regions of the oral cavity were cleaned.

At step 450 of the method, the obtained sensor data and/or imaging data is communicated to another personal care device. According to an embodiment, the network comprises a central hub 40 that facilitates the communication between two or more personal care devices within network 200.

At step 460 of the method, the other personal care devices within the network modifies one or more functions or parameters intended to correct a deficiency in the user's oral cleaning identified via the obtained sensor data, to improve overall cleaning, to ensure or improve adherence to a cleaning program or goal, and/or one or more other goals of the user, system, or an oral hygiene professional. As described or otherwise envisioned herein, the modification may be an increase in function to improve cleaning of a particular area of the mouth identified as having been under-cleaned, a prolonged cleaning, a notification to the user, and/or a wide variety of other modifications. For example, if the sensor data indicates that the cleaning session was too short, or that one of the personal care devices was not utilized, the modification may be to prolong a brushing time and/or to recommend the use of a mouthwash or other personal care device. According to an embodiment, the modification is performed automatically without any input from or notice to the user.

Although the invention may comprise one or more connected devices, it may also or alternatively comprise one or more non-connected devices with a communication add-on, such as a toothbrush with a Bluetooth or Wi-Fi add-on component. Although these devices may not comprise a sensor and thus do not obtain information about the user's cleaning routine or oral cavity, the devices can communicate to provide a notification or alert that promotes the proper cleaning routine or sequence.

Although most of the embodiments described herein are in reference to oral cleaning, it should be appreciated that the system can be utilized for other personal hygiene routines, such as shaving or washing the body. For example, a shaver may detect that a portion of the face or body was improperly shaved, and can communicate that information to a body trimmer to increase trimming at that location or portion. Many other systems and embodiments are possible.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A system for modifying a user's oral care program, the system comprising:
   a first personal care device adapted to perform an oral care function and configured to obtain sensor data for at least a portion of the user's oral cavity; and
   a second personal care device in communication with the first personal care device;
   wherein the second personal care device is configured to receive the obtained sensor data directly from the first personal care device, and further configured to modify, based on the obtained sensor data, a function of the second personal care device; and
   wherein an algorithm to modify personal care is used for analyzing the obtained sensor data and modifying the function of the second personal care device, and the modification is performed automatically without any input from or notice to the user.

2. The system of claim 1, further comprising a central hub configured to facilitate communication between the first personal care device and the second personal care device.

3. The system of claim 1, wherein said modification is made to correct a deficiency in the user's oral cleaning identified via the obtained sensor data.

4. The system of claim 1, wherein the obtained sensor data comprises information about a period of time since the first personal care device was used by the user.

5. A method for modifying a user's oral care program, the method comprising the steps of:
   providing a network of collaborative personal care devices comprising a first personal care device and a second personal care device, wherein the first personal care device is in communication with the second personal care device;
   cleaning at least a portion of the user's oral cavity using the first personal care device;
   obtaining, while cleaning with the first personal care device, sensor data for at least a portion of the oral cavity;
   communicating the obtained sensor data directly to the second personal care device; and
   modifying, based on the communicated sensor data, a function of the second personal care device, and wherein the modification is based on an algorithm to modify personal care by analyzing the obtained sensor data and the modification is made automatically by the second personal care device without any input from or notice to the user.

6. The method of claim 5, wherein said modification is made to correct a deficiency in the user's oral cleaning identified via the obtained sensor data.

7. The method of claim 5, further comprising a central hub configured to facilitate communication between the first personal care device and the second personal care device.

8. The method of claim 5, further comprising an imaging device configured to obtain one or more images of the oral cavity.

9. A method for modifying a user's oral care program, the method comprising the steps of:
   providing a network of collaborative personal care devices comprising a first personal care device, a second personal care device, and an imaging device, wherein the first personal care device is in communication with the second personal care device and the imaging device;
   obtaining an image of at least a portion of the user's oral cavity using the imaging device;
   cleaning the oral cavity with the first personal care device;
   obtaining sensor data for at least a portion of the oral cavity;
   communicating the obtained image to the second personal care device; and
   modifying, based on the communicated image and/or obtained sensor data, a function of the second personal care device, and wherein said modification is based on an algorithm to modify personal care by analyzing the obtained sensor data and the modification is made automatically by the first personal care device without any input from or notice to the user.

10. The method of claim 9, wherein said modification is made to correct a deficiency in the user's oral cleaning identified via the obtained image.

11. The method of claim 9, wherein the network further comprises a central hub configured to facilitate communication between the first personal care device and the imaging device.

* * * * *